United States Patent

[11] 4,456,613
[45] Jun. 26, 1984

Wang

[54] 6-KETO- AND 6-HYDROXY-8-AZAPROSTANOIDS AND ANTI-ULCER USE THEREOF

[75] Inventor: Chia-Lin J. Wang, Wilmington, Del.

[73] Assignee: E. I. Du Pont de Nemours and Company, Wilmington, Del.

[21] Appl. No.: 452,883

[22] Filed: Dec. 27, 1982

[51] Int. Cl.³ .................... A61K 31/40; C07D 207/27
[52] U.S. Cl. .................................... 424/274; 548/551
[58] Field of Search ................ 548/551; 542/442; 424/274

[56] References Cited

U.S. PATENT DOCUMENTS

| | | | |
|---|---|---|---|
| 3,873,566 | 3/1975 | Scribner | 548/367 |
| 4,003,911 | 1/1977 | Scribner | 548/544 |
| 4,115,401 | 9/1978 | Nanthavong et al. | 548/551 |
| 4,131,738 | 12/1978 | Smith | 560/121 |
| 4,156,092 | 5/1979 | Smith | 560/121 |
| 4,205,178 | 5/1980 | Axen | 560/121 |
| 4,320,136 | 3/1982 | Scribner | 548/551 |

FOREIGN PATENT DOCUMENTS 2742730  4/1978  Fed. Rep. of Germany ...... 548/551

Primary Examiner—Paul M. Coughlan, Jr.
Assistant Examiner—David B. Springer
Attorney, Agent, or Firm—James A. Costello

[57] ABSTRACT

Biologically active 6-keto- and 6-hydroxy-8-azaprostanoids having the formula:

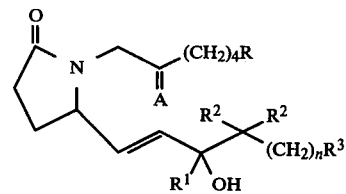

wherein
A is O or

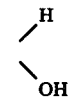

R is $CO_2R^4$ or $CH_2OH$;
$R^1$ is H, $CH_3$, or $C_2H_5$;
$R^2$ is H, $CH_3$, or F;
$R^3$ is $CH_3$ or $CF_3$;
$R^4$ is H, $C_1$ to $C_{12}$ n-alkyl, branched chain alkyl, or cycloalkyl, or a physiologically acceptable metal or amine salt cation; and
n is an integer from 3 to 8.

22 Claims, No Drawings

6-KETO- AND 6-HYDROXY-8-AZAPROSTANOIDS AND ANTI-ULCER USE THEREOF

BACKGROUND OF THE INVENTION

This invention concerns biologically active 6-keto-8-azaprostanoids and 6-hydroxy-8-azaprostanoids.

There are many references in the literature to prostanoids, a term which is generic to natural and synthetic prostaglandins and prostaglandin-like compounds. It is well known in connection with these prostanoids that even slight differences in chemical structures or stereochemical configurations will have profound effects on biological activity.

Prostanoids have a five-membered ring bearing relatively lengthy substituents on adjacent ring atoms. In most of the known prostanoids, the rings are carbocyclic. Representative of the prostanoids that contain a carbocyclic ring are those described in the following publications: U.S. Pat. No. 4,131,738, U.S. Pat. No. 4,156,092 and U.S. Pat. No. 4,205,178.

In some of the known carbocyclic ring prostanoids, one of the side chains is substituted in the C-16 position by two fluorine atoms. Representative of the publications which disclose carbocyclic-based 16,16-difluoroprostanoids are: Belgium Pat. No. 817,846 (Magerlein), U.S. Pat. No. 4,017,534 (Schaub et al.), U.S. Pat. No. 4,187,381 (Holland et al.), and Magerlein et al., *Prostaglandins*, 9 (4), 527 to 529 (1975).

U.S. Pat. No. 4,320,136 discloses 8-aza-16,16-difluoroprostanoids that differ from those of the prostanoids of this invention that are 16,16-difluoro-substituted primarily in the character of substituent A.

Other representative heterocycle-based prostanoids are the aza- and diaza-prostanoids disclosed in U.S. Pat. No. 3,873,566 (Scribner), U.S. Pat. No. 3,975,399 (De Franco and Scribner), U.S. Pat. No. 4,003,911 and U.S. Pat. No. 4,032,533 (Scribner), U.S. Pat. No. 4,113,873 (Himizu), U.S. Pat. No. 4,177,346 (Nelson), U.S. Pat. No. 4,211,876 (Scribner), and Belgium Pat. No. 854,268 (Hoechst).

The primary distinction between the prostanoids of this invention and those of the art lies in the character of the substitution (oxo or hydroxy) at the 6-position of an 8-azaprostanoid. This structural feature is believed to enhance the biological properties of the disclosed compounds, for example, as gastric cytoprotective agents that display anti-ulcer activity.

SUMMARY OF THE INVENTION

The compounds of this invention have the formula:

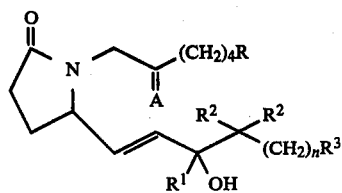

wherein
A is =O or

R is $CO_2R^4$ or $CH_2OH$;
$R^1$ is H, $CH_3$, or $C_2H_5$;
$R^2$ is H, $CH_3$, or F;
$R^3$ is $CH_3$ or $CF_3$;
$R^4$ is H, $C_1$ to $C_{12}$ n-alkyl, branched chain alkyl, or cycloalkyl, or a physiologically acceptable metal or amine salt cation; and
n is an integer from 3 to 8.

Preferred compounds are those wherein the stereochemical configuration is as follows:

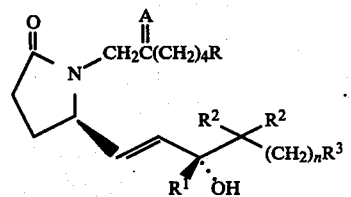

The most preferred compounds are those wherein A is =O or

R is $CO_2H$, $R^1$ and $R^2$ are each H; $R^3$ is $CH_3$ and n is 3. These compounds exhibit cytoprotective activity.

DETAILS OF THE INVENTION

Typical reaction conditions are provided in the Examples. It will be obvious that analogous conditions can be employed to make all of the compounds of this invention merely by employing appropriate reactants and the like. For instance, a different alkyl group R can be introduced by reaction 22 with the corresponding alcohol (ROH) in the presence of dicyclohexylcarbodiimide (DCC) and 4-dimethylaminopyridine (DMAP). Reaction of Compound 9 described in Example 1 with the anion derived from

by a procedure analogous to those described in the Examples will produce 23 and 24. Structures 22, 23 and 24 are:

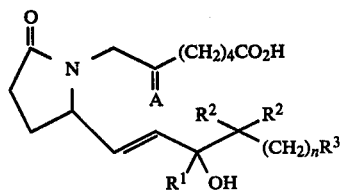

22

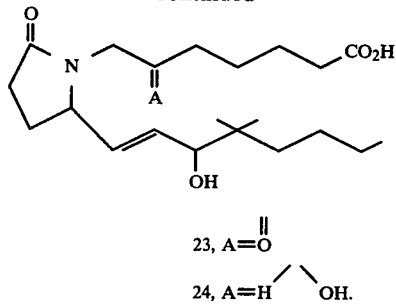

23, A=O
24, A=H/\OH.

UTILITY

Although a variety of animal models of antiulcer activity exist, most of the procedures were designed to detect compounds that inhibit gastric acid secretion. Tests of this type are not well suited for the study of a class of compounds that have some other mechanism of action. The naturally-occurring prostaglandins represent such a class. A recent focus of research has been to identify prostaglandin analogs that have antiulcer activity but do not have acid secretion influences.

The antiulcer model selected for screening of the azaprostanoids was the cytoprotection model. The cytoprotection model consists of: (a) administration of test compound to rats, (b) oral administration of absolute ethanol 1 hr later, and (c) sacrificing and evaluating the stomach for tissue damage (necrosis). The rationale of the cytoprotection model is that any compound that accelerates the stomach's own defense mechanisms, e.g., mucous production, will protect the tissues from damage caused by subsequent administration of a necrotizing agent such as strong acid or base, hypertonic salts, or ethanol.

Method

The subjects were male Sprague-Dawley rats (GIBCO) that were housed in the animal colony at least five days with ad lib food and water prior to fasting. The rats were deprived of all food 48 hrs prior to testing. The rats weighed 175 to 210 g when a test began.

Test compounds were prepared for injection 1 hr before a test by sonication for 20 sec in 0.05% sodium alignate solution. A stock solution of sodium alginate in water was prepared at least 24 hrs before use. Compounds were injected orally with a 16 gauge intubation probe (Tieman); the injected volume was 0.5 ml per 200 g of body weight and the concentration of compound was 2 mg/kg of body weight. The number of rats per group was 6 to 8. Control rats received vehicle. For drugs supplied in ethanolic solution or as formulations of finely divided silica gel (Syloid ®, Davison Company), the vehicle contains a comparable amount of ethanol or silica gel.

One hr after administration of test compound each rat received an oral injection of absolute ethanol with a volume of 1.0 ml per 200 g of body weight. One hr after ethanol administration the rats were sacrificed with $N_2$ gas, the stomachs were removed and cut along the greater curvature. The stomachs were washed in tap water to remove mucous and were refrigerated until they were scored, usually within 1 hr.

Scoring was done "blind" by one of two experienced raters. Each stomach was compared to a series of six standard photographs that depicted no necrosis (a score of zero) through complete mecrosis covering the entire (except antral) glandular portion of the stomach (a score of 5). A score was assigned to each stomach on this 0 to 5 scale with a minimum increment of 0.25. For example, a stomach judged to be greater than 1.0 but less than 1.5 in severity of tissue damage received a score of 1.25. After all stomachs were scored the percent protection caused by the test compound was calculated:

Percent protection =

$$100 - \left( \frac{\text{mean score of test group}}{\text{mean score of control group}} \times 100 \right)$$

For example, if a test group had a mean score of 1.25 and the control group had a mean score of 2.5, the percent protection was:

$$100 - \left( \frac{1.25}{2.5} \times 100 \right) = 50\%.$$

Results:

By the method described above, it was found that the preferred compounds of this invention, i.e., Compounds 14 and 15 provided 60 and 49 percent protection, respectively. Based on these results, it is concluded that all of the compounds of this invention would have useful cytoprotection activity which is indicative of usefulness in treating ulcers.

The attractiveness of these compounds for drug use is enhanced because they are effective when taken orally as well as by injection. Furthermore, unlike natural prostaglandins of the PGE type, the compounds are quite stable chemically; for example, they would have a long shelf-life and are stable in moderately strong acid or basic media. Finally, the compounds of this invention are inexpensive and easy to make relative to the natural prostaglandins and many of their derivatives.

As pharmaceutical compositions useful for treating animal or human subjects, the compounds of this invention can be formulated as tablets or in capsules for oral administration or in oils for administration by injection. A pharmaceutically acceptable carrier will also usually be employed therewith.

The following Examples illustrate the invention. Temperatures are in degrees Centigrade. Proton nuclear magnetic resonance (PMR) chemical shifts are reported in parts per million (δunits) relative to internal tetramethylsilane standard, i.e., a downfield shift is positive in sign. Coupling constants, J, are reported in Hertz (Hz).

EXAMPLE 1

Step A

6-Hexanolactol (2)

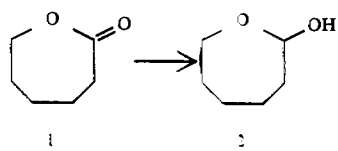

To a solution of 6-hexanolactone (1) (11.4 g, 0.1 mol) in methylene chloride (200 mL) at −78° was added diisobutylaluminum hydride (1.76M in toluene, 85 mL, 0.15 mol) slowly. The mixture was stirred at −78° for one hour and then poured into an ice-water mixture. After addition of 10% hydrogen chloride solution, the separated aqueous layer was extracted with methylene chloride and the combined organic layer was dried over magnesium sulfate. Removal of the solvent gave 6.3 g of 6-hexanolactol (2) which was dried by azeotroping with benzene and then subjected to the next reaction without purification.

Step B

6-Heptene-1-ol (3)

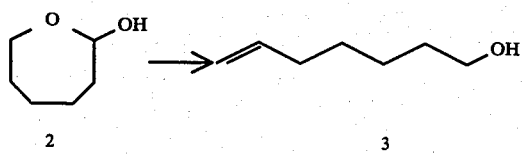

To a suspension of (methyl)triphenylphosphonium bromide (23.3 g, 65 mmol) in tetrahydrofuran (50 mL) at 0° was added n-butyllithium (1.6M in hexane, 49 mL, 78 mmol). The mixture was stirred at room temperature for 30 minutes. Then, a solution of 2 (6.3 g, 54 mmol) in tetrahydrofuran (30 mL) was added. The reaction mixture was stirred at room temperature overnight and then quenched with ice. After removing tetrahydrofuran in vacuo, the residue was taken up with petroleum ether and saturated aqueous ammonium chloride. The separated aqueous layer was extracted with ether-petroleum ether and the combined organic layer was washed with saturated aqueous sodium chloride and dried over magnesium sulfate. The crude product was purified by high performance liquid chromatography (HPLC) to afford 1.98 g of 6-heptene-1-ol (3). PMR (CDCl$_3$): δ6.20–4.80 (m, 3H), 3.64 (t, 2H), 2.25–1.20 (m, 9H).

Step C

7-Bromo-6-hydroxy-1-heptanol (4)

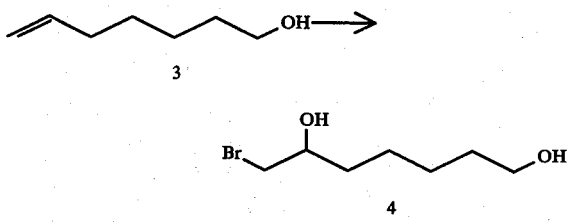

To a solution of 3 (500 mg, 4.38 mmol) in t-butanol-water (24 mL-4 mL) in the dark was added N-bromosuccinimide (NBS) (858 mg, 4.82 mmol) in small portions. Additional NBS (312 mg) was added after 4 hours and 16 hours later another 400 mg of NBS was added. The reaction mixture was stirred for 68 hours. After removal of t-butanol in vacuo, the residue was diluted with ether, washed with saturated sodium thiosulfite solution, saturated sodium chloride solution, and dried over magnesium sulfate. The crude product was purified by HPLC to give 123 mg of 7-bromo-6-hydroxy-1-heptanol (4).

Step D 6,7-Epoxy-1-heptanol (5)

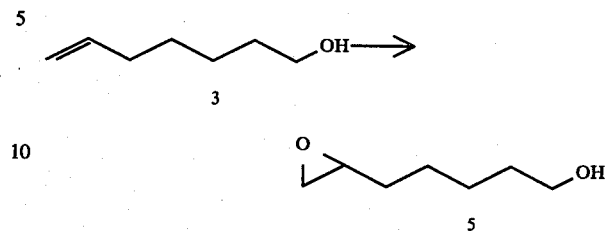

A mixture of 3 (1.4 g, 12 mmol) and m-chloroperbenzoic acid (2.92 g, 14.4 mmol) in methylene chloride (40 mL) was stirred at room temperature overnight. It was then diluted with ether, washed with saturated aqueous sodium bicarbonate, saturated aqueous sodium chloride, and dried over magnesium sulfate. Removal of the solvent afforded 1.64 g of the crude 6,7-epoxy-1-heptanol (5).

Step E

7-Bromo-6-hydroxy-1-heptanol (4)

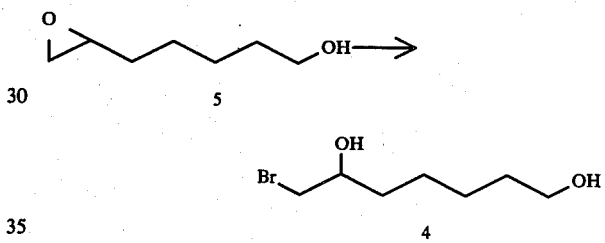

A mixture of 5 (120 mg, 0.9 mmol) in acetic acid-tetrahydrofuran (2 mL-0.4 mL) was treated with 0.3 mL of saturated aqueous potassium bromide solution at room temperature over 67 hours. It was then diluted with ether and poured into saturated aqueous sodium bicarbonate. The separated organic layer was washed with saturated sodium thiosulfite, saturated sodium chloride, and dried over magnesium sulfate. Evaporation of the solvent gave 127 mg of 7-bromo-6-hydroxy-1-heptanol (4).

In another run, the reaction was stirred at room temperature for 22 hours. One and one-half grams of 5 yielded 2.3 g of 4 which was combined with material from the previous run and purified by HPLC to give 0.72 g of pure 4. IR (neat): 3350 cm$^{-1}$; PMR (CDCl$_3$): δ3.90–3.30 (m, 7H, containing 2—OH), 1.80–1.25 (m, 8H).

Step F

7-Bromo-1,6-bistetrahydropyranyl heptanyl Ether

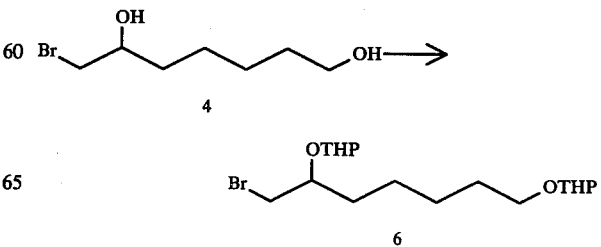

A solution of 4 (123 mg, 0.58 mmol) and dihydropyran (0.22 mL, 2.33 mmol) in methylene chloride (2 mL) containing pyridinium tosylate (25 mg, 0.1 mmol) was stirred at room temperature for 20 hours. It was diluted with ether and washed with saturated aqueous sodium chloride. The separated aqueous layer was extracted once with ether and the combined ether layer was dried over magnesium sulfate. The crude product was purified on a silica gel column to give 170 mg of 7-bromo-1,6-bistetrahydropyranyl heptanyl ether (6). PMR (CDCl₃): δ4.86–4.48 (m, 2H), 4.00–3.41 (m, 9H), 1.93–1.18 (m, 20H).

Step G 7-(2-Carbomethoxy-5-oxopyrrolidin-1-yl)-1,6-bistetrahydropyranyl heptanyl Ether (8)

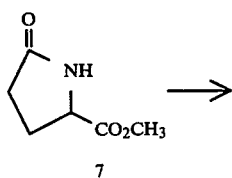

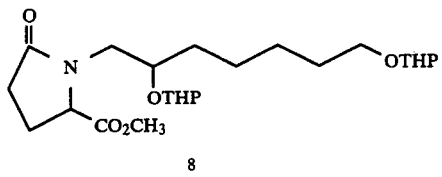

To a suspension of sodium hydride (59.6% oil dispersion, 53 mg, 1.3 mmol) in dimethylformamide (2 mL) was added a solution of methyl pyroglutamate (7) (187 mg, 1.3 mmol) and 6 (165 mg, 0.43 mmol) in dimethylformamide (2 mL). The reaction mixture was then heated at 80° for 21 hours. After quenching the reaction with ice, it was diluted with ether, washed with water, and dried over magnesium sulfate. The crude product was purified by silica gel column chromatography to give 57.8 mg of 7-(2-carbomethoxy-5-oxopyrrolidin-1-yl)-1,6-bistetrahydropyranyl heptanyl ether (8). IR (CH₂Cl₂): 1730, 1685 cm⁻¹; PMR (CDCl₃): δ4.53 (bs, 2H), 3.73 (S, 3H), 3.86–3.30 (m, 10H), and 2.50–1.25 (m, 24H); MS: m/z 357.2127 (M+), calcd. for $C_{18}H_{31}O_6N$, 357.2149.

Step H 7-(2-Formyl-5-oxopyrrolidin-1-yl)-1,6-bistetrahydropyranyl heptanyl ether (9)

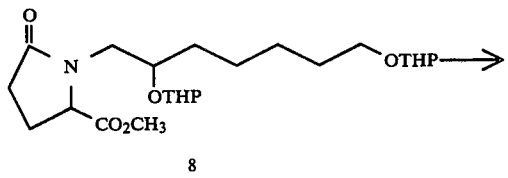

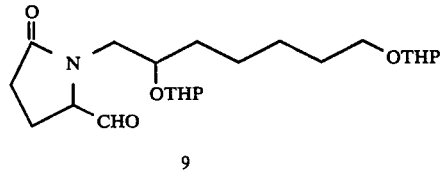

Following a procedure similar to that reported in U.S. Pat. No. 3,975,399 (DeFranco and Scribner), a solution of 8 (2 g, 4.52 mmol) in tetrahydrofuran (20 mL) at −78° was treated with a solution of 1.5 mL of Red-Al® (70% solution of sodium bis(2-methoxyethoxy)aluminum hydride in benzene) in tetrahydrofuran (4 mL). The mixture was stirred at −78° for 1.5 hours and poured into a mixture of ether and water. The separated organic layer was washed with water, saturated sodium chloride and dried over magnesium sulfate. Removal of the solvent gave 2.1 g of crude 7-(2-formyl-5-oxopyrrolidin-1-yl)-1,6-bistetrahydropyranyl heptanyl ether (9) which was directly submitted to the next reaction.

Step I

7-[2-(3-Oxo-1-octen-1-yl)-5-oxopyrrolidin-1-yl]-1,6-bistetrahydropyranyl heptanyl Ether (10)

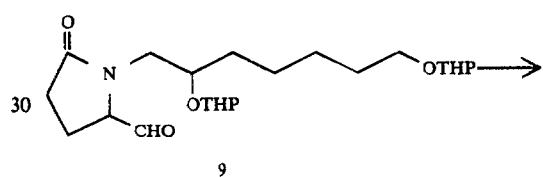

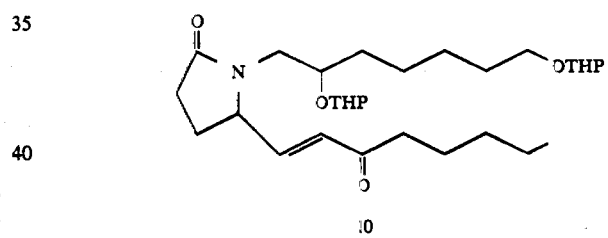

A solution of dimethy(2-oxoheptyl)phosphonate (1.094 g, 4.92 mmol) and sodium hydride (59.6% oil dispersion, 180 mg, 4.46 mmol) in glyme (ethylene glycol dimethyl ether, 40 ml) was stirred at room temperature for 30 minutes. Then, to the above mixture was added a solution of 9 (2.1 g) in glyme (20 ml). The reaction was stirred at room temperature for one hour before it was quenched with ice. Removal of the glyme in vacuo was followed by addition of ether, the ether layer was then washed with saturated sodium chloride and dried over magnesium sulfate. The crude product was purified by HPLC to give 2.33 g of 7-[2-(3-oxo-1-octen-1-yl)-5-oxopyrrolidin-1-yl]-1,6-bistetrahydropyranyl heptanyl ether (10): IR (CH₂Cl₂): 1690, 1640 cm⁻¹; PMR (CDCl₃): δ6.50 (m, 1H), 6.02 (m, 1H), 4.48 (m, 2H), 4.00–1.18 (m, 42H), and 0.86 (t, 3H); MS: m/z 339.2388 (M+—bisTHP), calcd. for $C_{19}H_{33}O_4N$, 339.2408.

Step J

7-[2-(3-Hydroxy-1-octen-1-yl)-5-oxopyrrolidin-1-yl]-1,6-bistetrahydropyranyl heptanyl Ether (11)

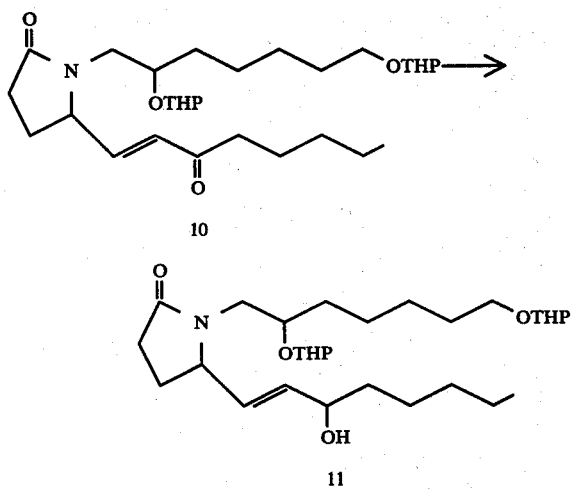

To a solution of 10 (1 g, 1.97 mmol) in ethanol (10 mL) at −20° was added sodium borohydride (85 mg, 2.2 mmol). The reaction mixture was stirred at −20° for 2.5 hours and then quenched with one drop of acetic acid. It was diluted with ether, washed with saturated aqueous sodium bicarbonate, saturated aqueous sodium chloride, and dried over magnesium sulfate. Removal of the solvent afforded 900 mg of 7-[2-(3-hydroxy-1-octen-1-yl)-5-oxopyrrolidin-1-yl]-1,6-bistetrahydropyranyl heptanyl ether (11). A separate sample of the product, prepared by essentially the foregoing procedure, was submitted for analysis. IR (CH$_2$Cl$_2$): 3500, 1690 cm$^{-1}$; PMR (CDCl$_3$): δ5.68–5.27 (m, 2H), 4.50 (bs, 2H), 4.13–3.25 (m, 10H), 2.43–1.18 (m, 33H), and 0.89 (t, 3H); MS: m/z 491.3567 (M$^+$—H$_2$O), calcd. for C$_{29}$H$_{49}$O$_5$N, 491.3608.

Step K

7-[2-(3-Acetoxy-1-octen-1-yl)-5-oxopyrrolidin-1-yl]-1,6-bistetrahydropyranyl heptanyl Ether (12)

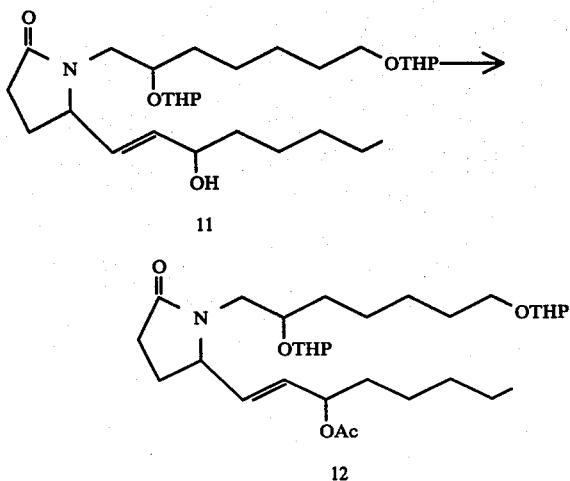

A mixture of 11 (900 mg, 1.76 mmol) in methylene chloride (10 mL) containing acetic anhydride (0.25 mL, 2.65 mmol), and 4-dimethylaminopyridine (25 mg, 0.2 mmol) was stirred at room temperature for two hours. It was then diluted with ether and washed with water and saturated sodium chloride solution. After drying over magnesium sulfate, the solvent was evaporated in vacuo to give 1.03 g of 7-[2-(3-acetoxy-1-octen-1-yl)-5-oxopyrrolidin-1-yl]-1,6-bistetrahydropyranyl heptanyl ether (12). IR (CH$_2$Cl$_2$): 1725, 1680 cm$^{-1}$; PMR (CDCl$_3$): δ5.55–5.07 (m, 2H), 4.59–2.22 (m, 15H), 2.05 (2S, 3H), 2.00–1.14 (m, 30H), and 0.91 (t, 3H). A separate sample of the product, prepared by essentially the foregoing procedure, was submitted for mass spectrometry. MS: m/z 491.3591 (M$^+$—HOAc), calcd. for C$_{29}$H$_{49}$O$_5$N, 491.3608.

Step L

7-[2-(3-Acetoxy-1-octen-1-yl)-5-oxopyrrolidin-1-yl]-6-oxo-1-heptanoic Acid (13)

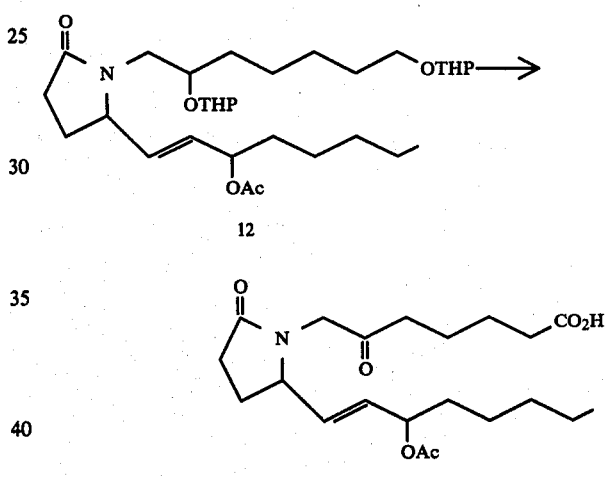

A solution of 12 (1.03 g, 1.76 mmol) in acetone (15 mL) at 0° was treated with excess Jones reagent. The mixture was stirred at 0° for one hour before it was quenched with 2-propanol. After removing the solvent in vacuo, the residue was taken up with ether and saturated aqueous sodium chloride. The separated aqueous layer was extracted with ether and the combined ether layer was washed with saturated sodium chloride. Removal of the solvent after drying over magnesium sulfate afforded 880 mg of the crude 7-[2-(3-acetoxy-1-octen-1-yl)-5-oxopyrrolidin-1-yl]-6-oxo-1-heptanoic acid (13). This crude product was combined with another one gram of crude 13 which was prepared by essentially the foregoing procedure and purified by HPLC to give 1 g of pure 13. IR (CH$_2$Cl$_2$): 3500–2500 (br), 1710 (br) cm$^{-1}$; PMR (CDCl$_3$): δ5.37 (m, 2H), 5.06 (m, 1H), 4.36–3.44 (m, 3H), 2.36 (m, 6H), 2.03 (S, 3H), 1.77–1.23 (m, 14H), and 0.87 (t, 3H); MS: m/z 335.2101 (M$^+$—HOAc), calcd. for C$_{19}$H$_{29}$O$_4$N, 335.2095.

Step M

7-[2-(3-Hydroxy-1-octen-1-yl)-5-oxopyrrolidin-1-yl]-6-oxo-1-heptanoic Acid (14)

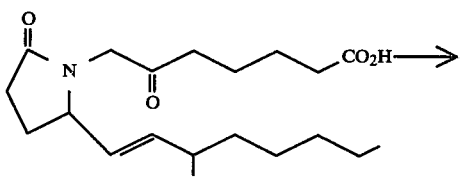

13

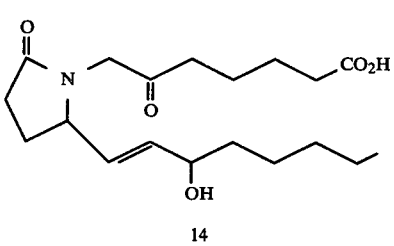

14

To a solution of 13 (100 mg, 0.25 mmol) in methanol (3 mL) was added potassium carbonate (220 mg, 1.59 mmol). The reaction mixture was stirred at room temperature for five hours before it was acidified with 10% hydrochloric acid to pH 2. It was then diluted with saturated aqueous sodium chloride and extracted with ether three times. The combined ether layer was washed with saturated sodium chloride and dried over magnesium sulfate. Removal of the solvent afforded 70 mg of 7-[2-(3-hydroxy-1-octen-1-yl)-5-oxopyrrolidin-1-yl]-6-oxo-1-heptanoic acid (14). IR (CH$_2$Cl$_2$): 3600–2500 (br), 1720, 1690 cm$^{-1}$; PMR (CDCl$_3$): δ5.67 (bs, 2H, —CO$_2$H and —OH), 5.67–5.17 (m, 2H), 4.33–3.56 (m, 4H), 2.57–2.13 (m, 6H), 1.90–1.07 (m, 14H), and 0.90 (t, 3H); MS: m/z 335 (M$^+$—H$_2$O).

EXAMPLE 2

7-[2-(3-Hydroxy-1-octen-1-yl)-5-oxopyrrolidin-1-yl]-6-hydroxy-1-heptanoic Acid (15)

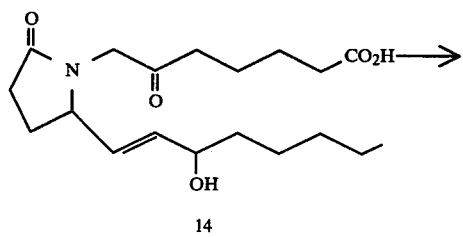

14

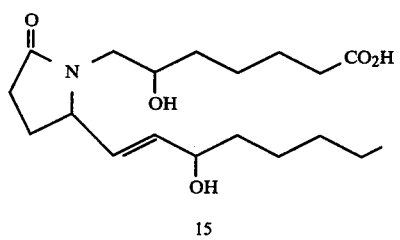

15

To a solution of 14 (over 100 mg) in 3 mL of ethanol at 0° was added 45 mg of sodium borohydride. After stirring two hours at 0°, it was quenched with a few drops of acetic acid. Saturated sodium chloride was added, followed by extraction with methylene chloride three times. The combined organic layer was then dried over magnesium sulfate. Removal of the solvent gave 140 mg of 7-[2-(3-hydroxy-1-octen-1-yl)-5-oxopyrrolidin-1-yl]-6-hydroxy-1-heptanoic acid (15). IR (CH$_2$Cl$_2$): 3500–2600 (br), 1720, 1665 cm$^{-1}$; PMR (CDCl$_3$): δ6.33–5.40 (m, 5H, including —CO$_2$H and 2—OH), 4.23–3.00 (m, 5H), 2.66–2.20 (m, 4H), 1.90–1.13 (m, 16H), and 0.93 (t, 3H); MS: m/z 338.2313 (M$^+$—OH), calcd. for C$_{19}$H$_{32}$O$_4$N, 338.2330.

EXAMPLE 3

7-[2-(3-Hydroxy-1-octen-1-yl)-5-oxopyrrolidin-1-yl]-1,6-heptanediol (16)

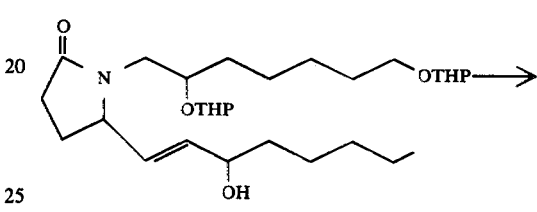

11

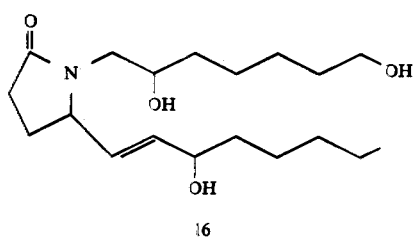

16

A solution of 11 (200 mg, 0.39 mmol) in acetic acid-tetrahydrofuran-water (1 mL-0.5 mL-0.5 mL) was heated at about 45° for two hours. It was then diluted with ether, washed with saturated sodium bicarbonate and saturated sodium chloride solutions and dried over magnesium sulfate. Removal of the solvent afforded 68 mg of 7-[2-(3-hydroxy-1-octen-1-yl)-5-oxopyrrolidin-1-yl]-1,6-heptanediol (16) after purification by silica gel column chromatography. IR (CH$_2$Cl$_2$): 3500, 1650 cm$^{-1}$; PMR (CDCl$_3$): δ5.73–5.39 (m, 2H), 4.11 (m, 2H), 3.73 (m, 1H), 3.61 (t, 2H), 3.55–3.00 (m, 2H), 2.61–2.11 (m, 5H, including 3—OH), 1.64–1.23 (m, 18H), and 0.89 (t, 3H); MS: m/z 323.2449 (M$^+$—H$_2$O), calcd. for C$_{19}$H$_{33}$O$_3$N, 323.2459.

EXAMPLE 4

Step A

7-[2-(3-Oxo-4,4-difluoro-1-octen-1-yl)-5-oxo-pyrrolidin-1-yl]-1,6-bistetrahydropyranyl heptanyl Ether (17)

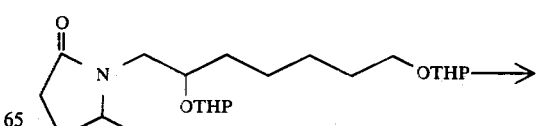

9

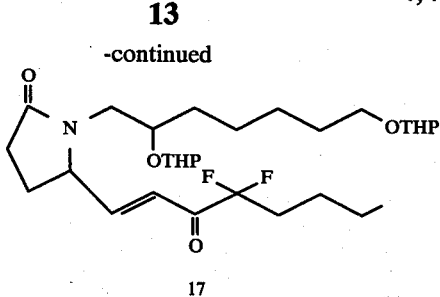

17

A solution of dimethyl (3,3-difluoro-2-oxo-heptyl-phosphonate (120 mg, 0.467 mmol) and sodium hydride (59.6% oil dispersion, 16 mg, 0.38 mmol) in glyme (ethylene glycol dimethyl ether, 3 mL) was stirred at room temperature for 30 minutes. Then, to the above mixture was added a solution of 9 (160 mg, 0.38 mmol) in glyme (2 mL). The reaction was stirred at room temperature for one hour followed by refluxing for another hour. After quenching with ice and removal of glyme in vacuo, the residue was diluted with ether and washed with saturated sodium chloride. The separated aqueous layer was extracted with ether twice and the combined ether layer was dried over magnesium sulfate. The crude product was purified on TLC plates to give 47 mg of 7-[2-(3-oxo-4,4-difluoro-1-octen-1-yl)-5-oxo-pyrrolidin-1-yl]-1,6-bistetrahydropyranyl heptanyl ether (17). IR (CH$_2$Cl$_2$): 1700 (br), 1640 cm$^{-1}$; PMR (CDCl$_3$): δ7.25–6.45 (m, 2H), 4.80–1.20 (m, 42H), and 0.90 (t, 3H).

Step B

7-[2-(3-Hydroxy-3-methyl-4,4-difluoro-1-octen-1-yl)-5-oxopyrrolidin-1-yl]-1,6-bistetrahydropyranyl heptanyl Ether (18)

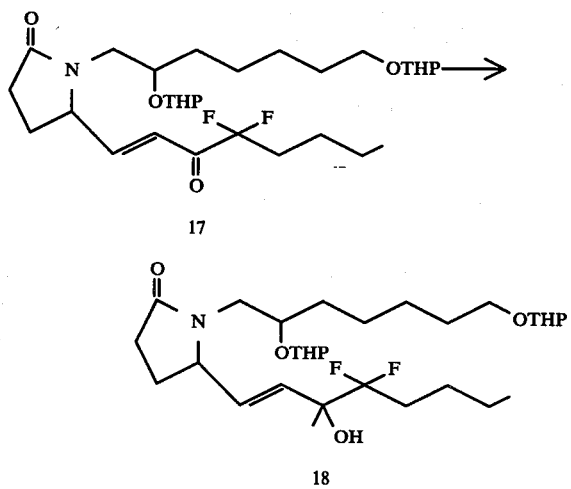

To a solution of 17 (21 mg, 0.038 mmol) in tetrahydrofuran (2 mL) at 0° was added methyl magnesium bromide (3.1M in ether, 0.04 mL, 0.114 mmol). The reaction mixture was stirred at 0° for one hour and then quenched with saturated ammonium chloride. It was subsequently diluted with ether, washed with saturated aqueous sodium chloride, and dried over magnesium sulfate. Removal of the solvent in vacuo afforded 19.2 mg of 7-[2-(3-hydroxy-3-methyl-4,4-difluoro-1-octen-1-yl)-5-oxopyrrolidin-1-yl]-1,6-bistetrahydropyranyl heptanyl ether (18) which was directly subjected to the next reaction without purification.

Step C

7-[2-(3-Hydroxy-3-methyl-4,4-difluoro-1-octen-1-yl)-5-oxopyrrolidin-1-yl]-1,6-heptanediol (19)

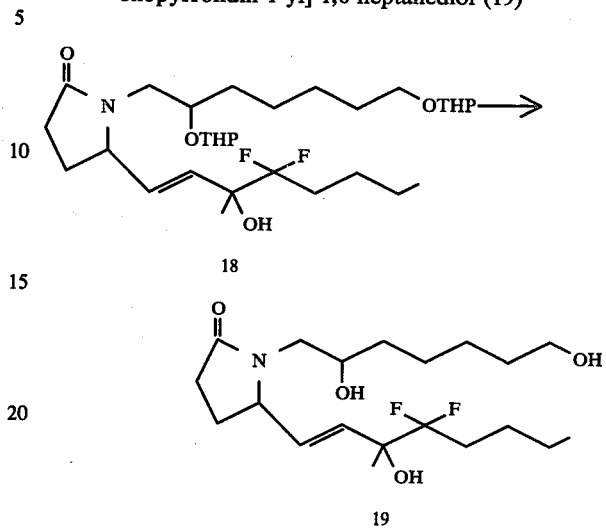

A mixture of 18 (19.2 mg) in acetic acid-tetrahydrofuran-water (1 mL-0.5 mL) was heated at about 45° for two hours. It was then diluted with ether, washed with saturated sodium bicarbonate and saturated sodium chloride solutions, and dried over magnesium sulfate. The crude product was purified on a TLC plate to give 2.4 mg of 7-[2-(3-hydroxy-3-methyl-4,4-difluoro-1-octen-1-yl)-5-oxopyrrolidin-1-yl]-1,6-heptanediol (19). PMR (CDCl$_3$): δ5.80 (m, 2H), 4.30–1.10 (m, 30H) and 0.92 (t, 3H). A separate sample of the product, prepared by essentially the foregoing procedure, was submitted for IR and mass spectrometry: IR (CH$_2$Cl$_2$): 3600–3100 (br), 1670 cm$^{-1}$; MS: m/z 373.2402 (M$^+$—H$_2$O), calcd. for C$_{20}$H$_{33}$NO$_3$F$_2$, 373.2428.

EXAMPLE 5

7-[2-(3-Hydroxy-3-methyl-4,4-difluoro-1-octen-1-yl)-5-oxopyrrolidin-1-yl]-6-oxoheptanoic Acid (20)

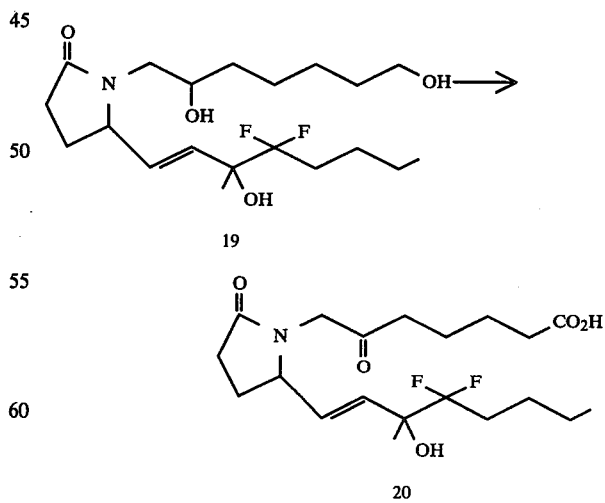

A mixture of 19 (37 mg, 0.09 mmol) in dimethylformamide (1 mL) containing pyridinium dichromate (165 mg, 0.45 mmol) was stirred at room temperature overnight. It was then poured into water and extracted with ether three times. The combined ether layer was washed with water and dried over magnesium sulfate. Removal of the solvent in vacuo gave 11.6 mg of 7-[2-(3-hydroxy-3-methyl-4,4-difluoro-1-octen-1-yl)-5-oxopyrrolidin-1-yl]-6-oxo-heptanoic acid (20). IR ($CH_2Cl_2$): 3600–2800 (br), 1730, 1690 $cm^{-1}$; PMR ($CDCl_3$); δ5.85–5.62 (m, 2H), 4.33–3.65 (m, 3H), 2.50–1.20 (m, 21H), and 0.92 (t,3H); MS: m/z 385.2048 ($M^+-H_2O$), calcd. for $C_{20}H_{29}NO_4F_2$, 385.2064.

EXAMPLE 6

7-[2-(3-Hydroxy-3-methyl-4,4-difluoro-1-octen-1-yl)-5-oxopyrrolidin-1-yl]-6-hydroxyheptanoic Acid (21)

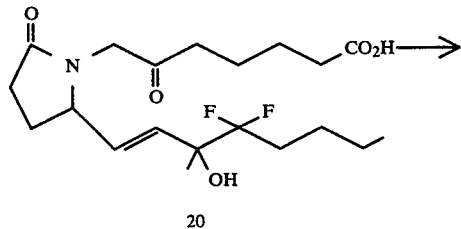

To a solution of 20 (24 mg, 0.059 mmol) in ethanol (2 mL) at 0° was added sodium borohydride (9 mg, 0.238 mmol). The reaction mixture was stirred at 0° for one hour before it was quenched with two drops of acetic acid. It was then diluted with saturated sodium chloride solution and extracted with chloroform three times. The combined organic layer was dried over magnesium sulfate. Purification of the crude product on TLC plates afforded 8 mg of 7-[2-(3-hydroxy-3-methyl-4,4-difluoro-1-octen-1-yl)-5-oxopyrrolidin-1-yl]-6-hydroxyheptanoic acid (21). IR ($CH_2Cl_2$): 3500–3200 (br), 1720, 1660 $cm^{-1}$; PMR ($CDCl_3$): δ5.95–5.60 (m, 2H), 4.40–2.80 (m, 4H), 2.60–1.20 (m, 21H), and 0.97 (t, 3H).

The embodiments of the invention in which an exclusive property or privilege is claimed are defined as follows:

1. A compound of the formula:

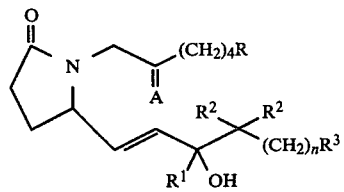

wherein
A is =O or

R is $CO_2R^4$ or $CH_2OH$;
$R^1$ is H, $CH_3$, or $C_2H_5$;
$R^2$ is H, $CH_3$, or F;
$R^3$ is $CH_3$ or $CF_3$;
$R^4$ is H, $C_1$ to $C_{12}$ n-alkyl, branched chain alkyl, or cycloalkyl, or a physiologically acceptable metal or amine salt cation; and
n is an integer from 3 to 8.

2. A compound according to claim 1 of the formula:

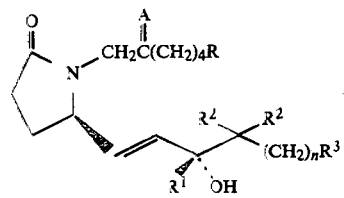

3. A compound according to claim 1 wherein A is =O or

R is $CO_2H$;
$R^1$ and $R^2$ are each H;
$R^3$ is $CH_3$; and
n is 3.

4. A compound according to claim 3 wherein A is =O.

5. A compound according to claim 3 wherein A is

6. A compound according to claim 1 wherein A is

R is $CH_2OH$;
$R^1$ and $R^2$ are each H;
$R^3$ is $CH_3$; and
n is 3.

7. A compound according to claim 1 wherein A is =O or

R is CH₂OH;

R¹ is H;

R² is F;

R³ is CH₃ and n is 3.

8. A compound according to claim 7 wherein A is =O.

9. A compound according to claim 7 wherein A is

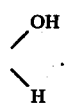

10. A compound according to claim 2 wherein A is =O or

R is CO₂H;

R¹ and R² are each H;

R³ is CH₃; and n is 3.

11. A compound according to claim 10 wherein A is =O.

12. A compound according to claim 10 wherein A is

13. A compound according to claim 2 wherein A is

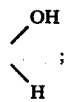

R is CH₂OH;

R¹ and R² are each H;

R³ is CH₃; and n is 3.

14. A compound according to claim 2 wherein A is =O or

R is CH₂OH;

R¹ is H;

R² is F;

R³ is CH₃ and n is 3.

15. A compound according to claim 14 wherein A is =O.

16. A compound according to claim 14 wherein A is

17. A physiologically acceptable metal salt of a compound according to claim 1.

18. A physiologically acceptable metal salt of a compound according to claim 2.

19. A physiologically acceptable amine salt of a compound according to claim 1.

20. A physiologically acceptable amine salt of a compound according to claim 2.

21. A pharmaceutical composition having cytoprotective activity comprising an effective amount of a compound according to claim 1 with a pharmaceutically acceptable carrier.

22. A method for preventing or treating ulcers in a human or an animal which comprises administering an effective amount of a pharmaceutical composition according to claim 21.

* * * * *